(12) United States Patent
Williams et al.

(10) Patent No.: US 6,821,325 B1
(45) Date of Patent: Nov. 23, 2004

(54) MULTI-SURFACE ANTI-BACTERIAL PROTECTIVE DEVICE

(76) Inventors: Jeffrey D. Williams, P.O. Box 143, Maricopa, CA (US) 93252; Bob D. Archibald, P.O. Box 143, Maricopa, CA (US) 93252

( * ) Notice: Subject to any disclaimer, the term of this patent is extended or adjusted under 35 U.S.C. 154(b) by 201 days.

(21) Appl. No.: 10/104,938

(22) Filed: Mar. 25, 2002

(51) Int. Cl.[7] ................................. C09D 5/14
(52) U.S. Cl. .................. 106/15.05; 106/2; 206/738; 206/742; 206/297; 206/527; 206/521.6; 206/521.15; 220/470; 220/476; 220/23.2; 220/33.4; 220/23.8; 424/402; 424/403; 424/404; 424/405; 424/406; 442/123; 442/124; 442/125
(58) Field of Search .................. 106/2, 15.05; 206/738, 206/742, 297, 527, 521.6, 521.15; 220/23.2, 33.4, 23.8, 470, 476; 424/402, 403, 404, 405, 406; 442/123, 124, 125

(56) References Cited

U.S. PATENT DOCUMENTS

| | | | | |
|---|---|---|---|---|
| 5,648,399 A | * | 7/1997 | Friedman et al. | 514/772.6 |
| 5,776,493 A | * | 7/1998 | Barclay et al. | 424/468 |
| 5,824,407 A | * | 10/1998 | Hayashi et al. | 428/318.8 |
| 5,869,096 A | * | 2/1999 | Barclay et al. | 424/468 |
| 6,455,030 B2 | * | 9/2002 | Saito et al. | 424/49 |
| 6,638,904 B2 | * | 10/2003 | White et al. | 512/27 |
| 2001/0044249 A1 | * | 11/2001 | Demott et al. | 442/304 |
| 2002/0022427 A1 | * | 2/2002 | Curro et al. | 442/373 |
| 2002/0192268 A1 | * | 12/2002 | Alwattari et al. | 424/443 |
| 2003/0064189 A1 | * | 4/2003 | Berg et al. | 428/40.1 |
| 2004/0020799 A1 | * | 2/2004 | Panella | 206/278 |

FOREIGN PATENT DOCUMENTS

JP        2000201945 A   *   8/2000   .......... B29C/33/14

* cited by examiner

Primary Examiner—Arti R. Singh

(57) ABSTRACT

A multi-surface anti-bacterial protective device for preventing transferring of bacteria from one person to another. The multi-surface anti-bacterial protective device includes a multi-layered material capable of being rolled up and also being capable of being severed into multi-layered pieces of material and also being adapted to fastenably cover a surface such as a light switch plate and a door knob; and also includes an anti-bacterial solution being disposed in the multi-layered material.

3 Claims, 2 Drawing Sheets

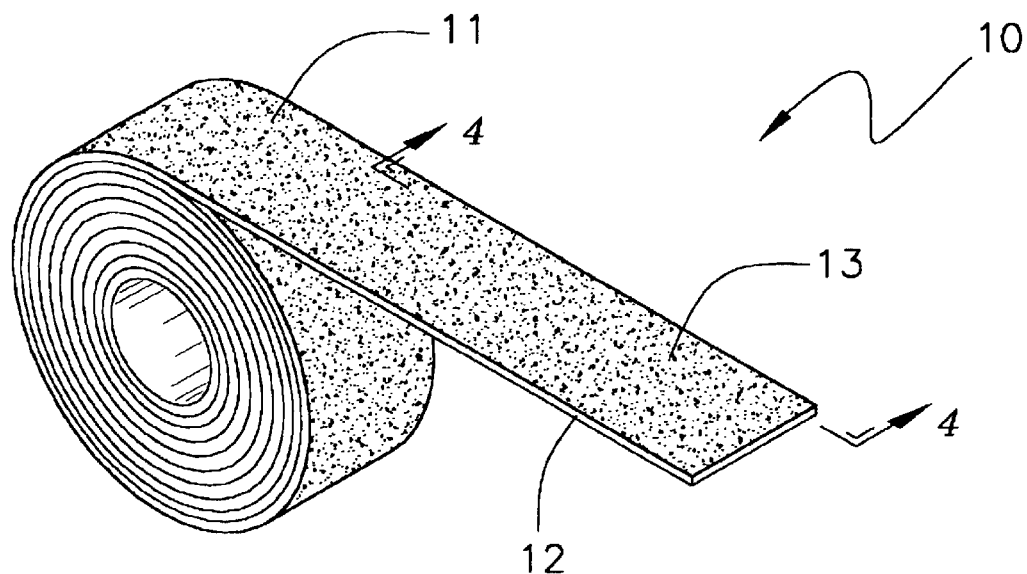
FIG. 1
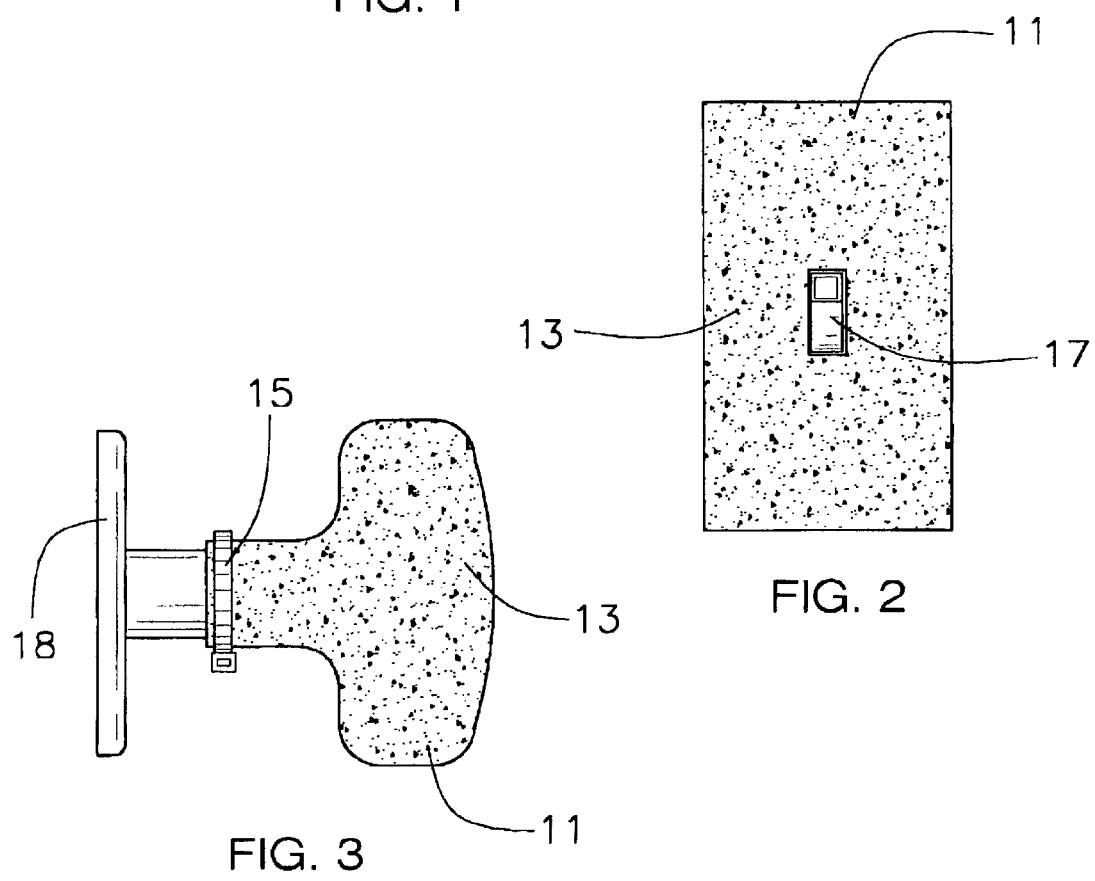
FIG. 2
FIG. 3

MULTI-SURFACE ANTI-BACTERIAL PROTECTIVE DEVICE

BACKGROUND OF THE INVENTION

1. Field of the Invention

The present invention relates to multi-surface anti-bacterial protectors and more particularly pertains to a new multi-surface anti-bacterial protective device for preventing transferring of bacteria from one person to another.

2. Description of the Prior Art

The use of multi-surface anti-bacterial protectors is known in the prior art. More specifically, multi-surface anti-bacterial protectors heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,856,140; U.S. Pat. No. 4,953,703; U.S. Pat. No. 4,008,351; U.S. Pat. No. 6,073,274; U.S. Pat. No. 5,987,645; and U.S. Pat. No. Des. 211,398.

While these devices fulfill their respective, particular objectives and requirements, the aforementioned patents do not disclose a new multi-surface anti-bacterial protective device. The prior art includes inventions having covers which are impregnated with disinfectants.

SUMMARY OF THE INVENTION

The general purpose of the present invention, which will be described subsequently in greater detail, is to provide a new multi-surface anti-bacterial protective device which has many of the advantages of the multi-surface anti-bacterial protectors mentioned heretofore and many novel features that result in a new multi-surface anti-bacterial protective device which is not anticipated, rendered obvious, suggested, or even implied by any of the prior art multi-surface anti-bacterial protectors, either alone or in any combination thereof. The present invention includes a multi-layered material capable of being rolled up and also being capable of being severed into multi-layered pieces of material and also being adapted to fastenably cover a surface such as a light switch plate and a door knob; and also includes an anti-bacterial solution being disposed in the multi-layered material. None of the prior art describes an invention having a cavity containing anti-bacterial solutions which seep through a permeable layer of material.

There has thus been outlined, rather broadly, the more important features of the multi-surface anti-bacterial protective device in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is an object of the present invention to provide a new multi-surface anti-bacterial protective device which has many of the advantages of the multi-surface anti-bacterial protectors mentioned heretofore and many novel features that result in a new multi-surface anti-bacterial protective device which is not anticipated, rendered obvious, suggested, or even implied by any of the prior art multi-surface anti-bacterial protectors, either alone or in any combination thereof.

Still another object of the present invention is to provide a new multi-surface anti-bacterial protective device for preventing transferring of bacteria from one person to another.

Still yet another object of the present invention is to provide a new multi-surface anti-bacterial protective device that is easy and convenient to quickly fasten to surfaces where bacterial are likely to be transferred.

Even still another object of the present invention is to provide a new multi-surface anti-bacterial protective device that provides a protective barrier against the transmission of contagious diseases through contact with common surfaces.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a new multi-surface anti-bacterial protective device according to the present invention.

FIG. 2 is a front elevational view of the present invention shown in use.

FIG. 3 is a side elevational view of the present invention shown in use.

DESCRIPTION OF THE PREFERRED EMBODIMENT

Figure 4:
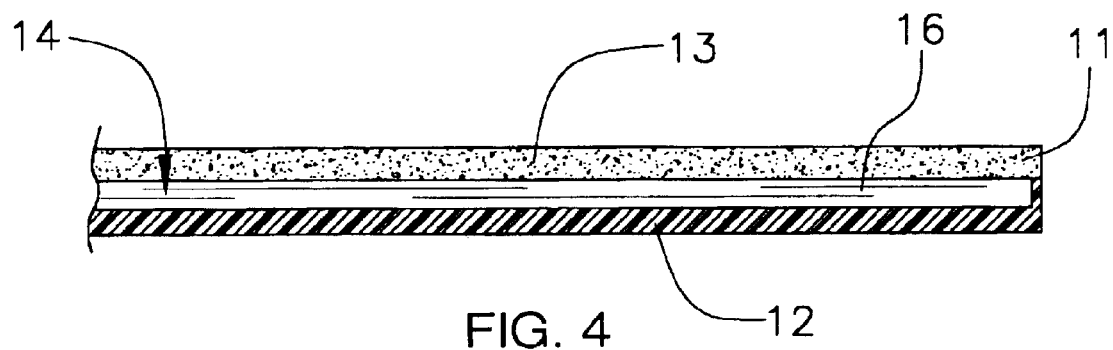
FIG. 4 is a cross-sectional view of the present invention.
Figure 5:
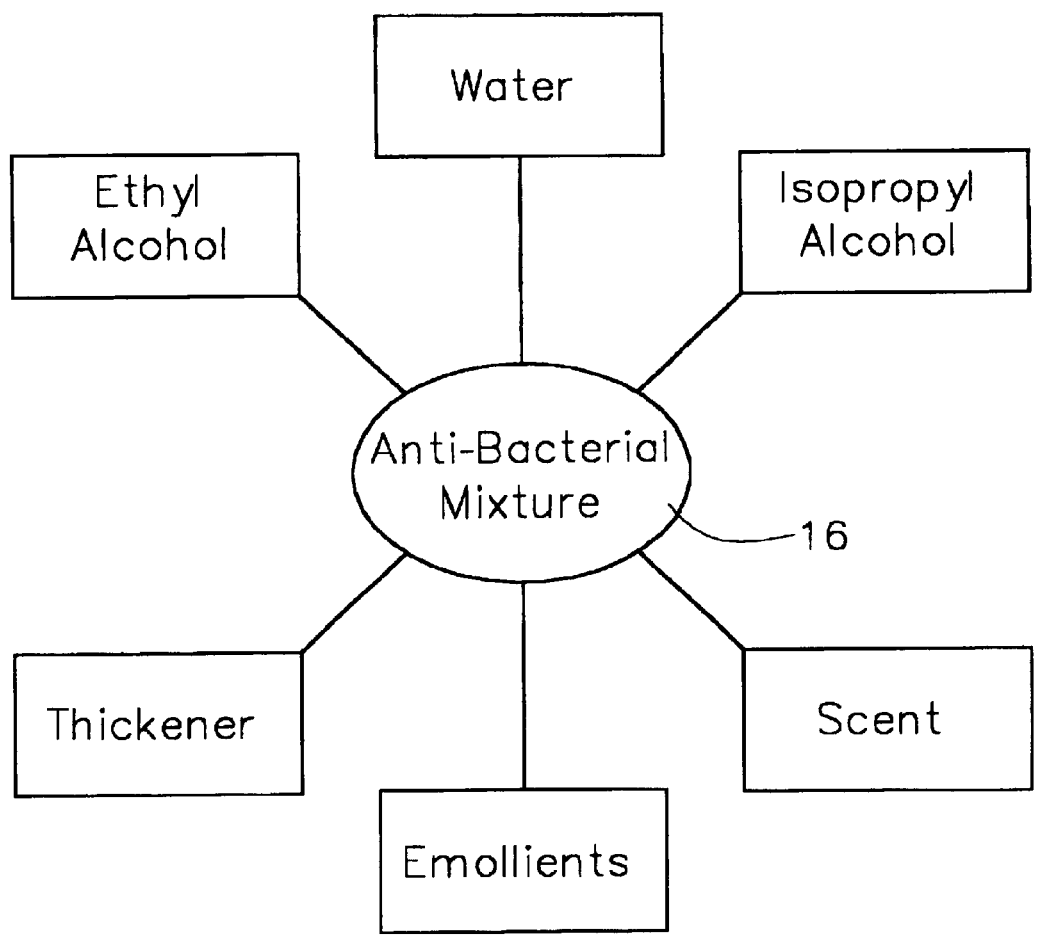
FIG. 5 is a schematic view of the anti-bacterial solution of the present invention.

With reference now to the drawings, and in particular to FIGS. 1 through 5 thereof, a new multi-surface anti-bacterial protective device embodying the principles and concepts of the present invention and generally designated by the reference numeral 10 will be described.

As best illustrated in FIGS. 1 through 5, the multi-surface anti-bacterial protective device 10 generally comprises a multi-layered material 11 capable of being rolled up and also being capable of being severed into multi-layered pieces of material and also being adapted to fastenably cover with a conventional fastener 15 upon a surface such as a light switch plate 17 and a door knob 18. The multi-layered material 11 includes an under layer of material 12 and an over layer of material 13, and also includes a cavity 14 being disposed in the multi-layered material 11 and substantially extending a length and width of said multi-layered material 11. The under layer of material 12 is made of non-permeable material, and the over layer of material 13 is made of permeable material.

An anti-bacterial solution 16 is disposed in the multi-layered material 11. The anti-bacterial solution 16 is disposed in the cavity 14 and seeps through the permeable material of the over layer of material 13. The anti-bacterial solution 16 includes (a) water, (b) ethyl alcohol, (c) isopropyl alcohol, (d) a conventional thickening agent, (e) conventional emollients, and (f) a conventional aromatic agent. The anti-bacterial solution 16 further includes (a) water in an amount of between 25% to 75% by volume, (b) ethyl alcohol in an amount of between 10% to 25% by volume, (c) isopropyl alcohol in an amount of between 10% to 2.5% by volume, (d) the conventional thickening agent in an amount of less than 5% by volume, (e) the conventional emollients in an amount of less than 5% by volume, and (f) the conventional aromatic agent in an amount of less than 2% by volume.

In use, the user severs a selected piece of multi-layered material 11 from a roll thereof and places the under layer of material 12 upon the potential bacterial-transmitting surface using a conventional fastener 15. As the user grasps or touches the surface, the anti-bacterial solution 16 seeps from the cavity 14 through and onto the over layer of material 13 which kills any bacteria that may have been deposited upon the surface of the over layer of material 13. After a period of time, when no more anti-bacterial solution 16 is contained in the cavity 14, the user can replace the multi-layered material 11 with another one.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the multi-surface anti-bacterial protective device. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A multi-surface antibacterial protective device comprising:

a multi-layered material capable of being rolled up and also being severable into multi-layered pieces of material and also fastenably covering a surface such as a light switch plate and a door knob; said multi-layered material including an under layer of material and an over layer of material, and also including a cavity being disposed in said multi-layered material, said under laver of material being made of non-permeable material, and said over laver of material being made of permeable material; and an anti-bacterial solution being disposed in said multi-layered material, said anti-bacterial solution being disposed in said cavity and seeping through said permeable material of said over layer.

2. A multi-surface anti-bacterial protective device as described in claim 1, wherein said anti-bacterial solution includes (a) water, (b) ethyl alcohol, (c) isopropyl alcohol, (d) a thickening agent, (e) emollients, and (f) an aromatic agent.

3. A multi-surface anti-bacterial protective device as described in claim 2, wherein said anti-bacterial solution further includes (a) said water in an amount of between 25% to 75% by volume, (b) said ethyl alcohol in an amount of between 10% to 25% by volume, (c) said isopropyl alcohol in an amount of between 10% to 25% by volume, (d) said thickening agent in an amount of less than 5% by volume, (e) said emollients in an amount of less than 5% by volume, and (f) said aromatic agent in an amount of less than 2% by volume.

\* \* \* \* \*